US006458751B1

(12) United States Patent
Abbas et al.

(10) Patent No.: US 6,458,751 B1
(45) Date of Patent: Oct. 1, 2002

(54) SKIN CLEANSING BAR COMPRISING A FATTY ALCOHOL WITH LOW MUSH

(75) Inventors: Syed Husain Abbas, Symour, CT (US); Ray Hui, College Point, NY (US); Laurie Ann Coyle, Park Ridge, NJ (US)

(73) Assignee: Unilever Home & Personal Care USA, Greenwich, CT (US)

( * ) Notice: Subject to any disclaimer, the term of this patent is extended or adjusted under 35 U.S.C. 154(b) by 0 days.

(21) Appl. No.: 09/911,037

(22) Filed: Jul. 23, 2001

(51) Int. Cl.[7] ............................ A61K 7/50; C11D 7/50

(52) U.S. Cl. ...................... 510/141; 510/152; 510/153; 510/155; 510/156

(58) Field of Search ................................ 510/141, 152, 510/153, 155, 156

(56) References Cited

U.S. PATENT DOCUMENTS

| | | | | | |
|---|---|---|---|---|---|
| 3,951,842 | A | | 4/1976 | Prince et al. | |
| 4,260,507 | A | * | 4/1981 | Barrett | 252/121 |
| 5,372,751 | A | | 12/1994 | Rys-Cicciari et al. | |
| 5,691,287 | A | | 11/1997 | Villars et al. | |
| 5,994,281 | A | | 11/1999 | He et al. | |
| 6,218,348 | B1 | * | 4/2001 | Aronson et al. | 510/153 |
| 6,248,803 | B1 | * | 6/2001 | Finucane et al. | 510/152 |
| 6,255,265 | B1 | * | 7/2001 | Van Gunst et al. | 510/152 |

FOREIGN PATENT DOCUMENTS

| | | |
|---|---|---|
| WO | 95/02035 | 1/1995 |

* cited by examiner

*Primary Examiner*—Necholus Ogden
(74) *Attorney, Agent, or Firm*—Alan A. Bornstein

(57) ABSTRACT

A cleansing bar composition is described comprising an anionic surfactant, a C6 to C18 free fatty acid, and a fatty alcohol having a melting point under about 35°C. and optionally a hydrophobic emollient. Useful emolients include triglycerides, hydrocarbons, silicones, fatty esters, and mixtures thereof. Useful anionic surfactants include C8 to C18 alkali metal acyl isethionates. Suitable low melting fatty alcohols include lauryl alcohol, oleyl alcohol, and a mixture thereof. The inventive bars have excellent mush, lather and wear properties.

18 Claims, No Drawings

SKIN CLEANSING BAR COMPRISING A FATTY ALCOHOL WITH LOW MUSH

BACKGROUND OF THE INVENTION

1. Field of the Invention

This invention relates generally to cleansing bars, and more particularly to cleansing bars having low mush. Synthetic detergent or syndet toilet bars have found considerable use as mild cleansing bars but such bars have the potential to exhibit unacceptable mush levels. Furthermore, syndet melt cast formulations require a higher level of solubilizers and suspending or dispersing agents than extruded formulations to dissolve all the components of the formulation. These solubilizers, such as fatty alcohols disadvantageously increase the mush level of the bar.

2. The Related Art

U.S. Pat. No. 5,691,287 issued to Villars et al. on Nov. 25, 1997 discloses a sodium cocoyl isethionate cleansing bar containing cetyl and stearyl alcohol in a total concentration range of about 6 to 11 wt percent.

U.S. Pat. No. 5,372,751 issued to Rys-Cucciari et al. on Dec. 13, 1994 discloses an acyl isethionate cleansing bar containing free fatty alcohols of 8–22 carbon atoms in an amount of 0–10 wt. percent.

U.S. Pat. No. 5,994,281 issued to He et al. on Nov. 30, 1999 discloses an acyl isethionate cleansing bar containing fatty alcohols of 16 to 22 carbon atoms.

PCT publication No. WO 95/02035 to Chambers et al., published on Jan. 19, 1995 discloses a fatty acid soap bar with minor amounts of acyl isethionates and fatty alcohols of 16 to 22 carbon atoms.

The above patents and publications however, fail to disclose or suggest a specific range of either alkyl alcohols of 6 to 12 carbon atoms or alkenyl alcohols of 6 to 18 carbon atoms in a cleansing bar composition which unexpectedly decreases mush, increases hardness, and has excellent lather; especially for syndet formulations.

SUMMARY OF THE INVENTION

The present invention relates to a cleansing bar composition comprising an anionic surfactant, a C6 to C18 free fatty acid, and a fatty alcohol selected from a C6 to C12 alkyl alcohol; and a C6 to C18 alkenyl alcohol wherein the melting point of the alcohol is under about 35 C. Preferably the anionic surfactant is in the concentration range of about 5 to about 60 weight % and the C6 to C18 free fatty acid is in the concentration range of about 2 to about 40 weight %.

The inventive cleansing bar also preferably contains a hydrophobic emollient. Advantageously this emollient is in the concentration range of about 2 to about 40 weight % and is selected from triglycerides, hydrocarbons, silicones, fatty esters, and mixtures thereof. The anionic surfactant preferably includes a C8 to C18 alkali metal acyl isethionate, and the free fatty acid preferably includes 12-hydroxy stearic acid. Advantageously, the fatty alcohol includes an alcohol selected from lauryl alcohol, oleyl alcohol, and a mixture thereof.

DETAILED DESCRIPTION OF THE INVENTION

The present invention relates to cleansing bar composition comprising:

a. an anionic surfactant in the concentration range of about 5 to about 60 weight %;

b. a C6 to C18 free fatty acid in the concentration range of about 2 to about 40 weight %; and c. a fatty alcohol selected from a C6 to C12 alkyl alcohol; and a C6 to C18 alkenyl alcohol wherein the melting point of the alcohol is under about 35° C.

Preferably the cleansing bar further comprises a hydrophobic emollient in the concentration range of about 0.5 to about 40 weight %. More preferably the hydrophobic emollient is in the concentration range of about 15 to about 25 weight %. Most preferably the hydrophobic emollient is selected from triglycerides, hydrocarbons, silicones, fatty esters, and mixtures thereof.

The cleansing bar preferably contains an anionic surfactant in the concentration range of about 25 to about 55 weight %; a C6 to C18 free fatty acid in the concentration range of about 15 to about 25 weight %; and the melting point of the fatty alcohol is under about 25° C.

Preferably the anionic surfactant includes a C8 to C18 alkali metal acyl isethionate. More preferably, the anionic surfactant includes a C8 to C12 alkali metal acyl isethionate. Preferably the alkali metal acyl isethionate is in the concentration range of about 5 to about 45 weight %, more preferably about 15 to about 25 weight %. Advantageously, the alkali metal acyl isethionate includes sodium cocoyl isethionate.

Conventional structuring agent free fatty acids are used in the bar. Preferably the free fatty acid includes 12-hydroxy stearic acid. Preferably the 12-hydroxy stearic acid is in the concentration range of about 5 to about 20 weight %, more preferably about 10 to about 15 weight %.

Preferably the fatty alcohol is a C6 to C12 alkyl alcohol. More preferably the fatty alcohol includes an alcohol selected from lauryl alcohol, oleyl alcohol, and a mixture thereof. Preferably the fatty alcohol is in the concentration range of about 2 to about 20 weight %, more preferably about 4 to about 8 weight %.

Surfactants:

Surfactants are an essential component of the inventive toilet bar. They are compounds that have hydrophobic and hydrophilic portions that act to reduce the surface tension of the aqueous solutions they are dissolved in. Useful surfactants can include anionic, nonionic, amphoteric, and cationic surfactants, and blends thereof.

Anionic Surfactants:

The toilet bar of the present invention contains one or more anionic detergents. The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$RO(CH_2CH_2O)_nSO_3M$ wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates, and the like.

Sulfosuccinates may be monoalkyl sulfosuccinates having the formula:

$R^4O_2CCH_2CH(SO_3M)CO_2M$; and amide-MEA sulfosuccinates of the formula;

$R^4CONHCH_2CH_2O_2CCH_2CH(SO_3M)CO_2M$ wherein $R^4$ ranges from $C_8$–$C_{22}$ alkyl and M is a solubilizing cation.

Sarcosinates are generally indicated by the formula:

$R^1CON(CH_3)CH_2CO_2M$, wherein $R^1$ ranges from $C_8$–$C_{20}$ alkyl and M is a solubilizing cation.

Taurates are generally identified by formula:

$R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

The inventive bar contains anionic surfactants, preferably contains $C_8$–$C_8$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Total surfactants will generally range from about 5% to about 60% by weight of the toilet bar. Preferably, this component is present from about 25% to about 40% in the bar.

The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

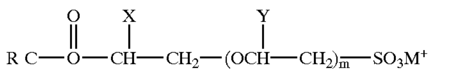

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

It should be understood that the bar may comprise a certain amount of soap as anionic surfactant. When used, the term "soap" is used in its popular sense, i.e., alkalimetal or alkanol ammonium salt of aliphatic alkane or alkene monocarboxylic acids. Sodium, potassium, mono-, di- and triethanol ammonium cations, or combinations thereof, are suitable for purposes of the invention. Generally, sodium soaps are used. Soaps useful herein are the well known alkali metal salts of natural or synthetic aliphatic (alkanoic or alkenoic) acids having 13 to 22 carbons, preferably 12 to 18. They may be described as alkali metal carboxylates of acrylic hydrocarbons having about 12 to 22 carbons.

Anionic surfactants with Krafft points of up to 40 to 45 ° C. can be used in the formulation. Anionic surfactants with a Krafft point below room temperature are preferred.

Amphoteric Surfactants

One or more amphoteric surfactants may be used in this invention. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

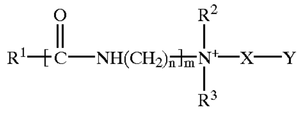

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $—CO_2—$ or $—SO_3—$

Suitable amphoteric surfactants within the above general formula include simple betaines of formula:

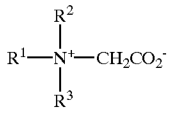

and amido betaines of formula:

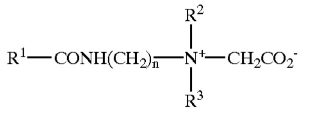

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

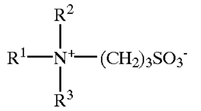

or

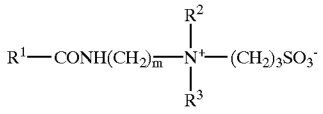

where m is 2 or 3, or variants of these in which $—(CH_2)_3SO_3^-$ is replaced by

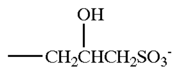

In these formulae $R^1$, $R^2$ and $R^3$ are as discussed previously.

Nonionic Surfactants

One or more nonionic surfactants may also be used in the toilet bar of the present invention.

The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic Surfactants

One or more cationic surfactants may also be used in the inventive toilet bar.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry & Berch, both of which are also incorporated into the subject application by reference.

Structuring Agents

The inventive toilet bar also contains 2 to 40% by wt., preferably 15 to 25% by wt. of total structurant $C_6$–$C_{18}$ free fatty acid. Preferably the structurant in the toilet bar includes 12-hydroxystearic acid. Structurants are used to enhance the bar integrity, improve the processing properties, and enhance desired user sensory profiles. Suitable co-structurants are generally long chain, preferably straight and saturated, ($C_8$–$C_{18}$) fatty acid or ester derivatives thereof; and/or branched long chain, preferably straight chain and saturated, ($C_{13}$–$C_{24}$) alkyl alcohol, or $C_{19}$–$C_{24}$ alkenyl- alcohol or mixtures thereof, or ether derivatives thereof. These co-structurants are preferably present at a level that allows the pH of the bar to remain in the 4.5 to 8.0 range, more preferably in the 5.0 to 6.0 range. The pH of the formulation may be adjusted by incorporating sodium or potassium salts of fatty acids. However, it is preferred not to neutralize 12-hydroxystearic acid if it is used as the sole structuring agent.

The inventive bar also optionally contains fillers selected from inorganic minerals such as calcium sulfate, and the like; and starches, preferably water soluble starches such as maltodextrin and the like and polyethylene wax or paraffin wax, and the like. Fillers may be present in the inventive toilet bar in the range of 1 to 15% by weight, preferably 1 to 5% by weight.

Other co-structuring aids can also be selected from water soluble polymers chemically modified with a hydrophobic moiety or moieties, for example, EO-PO block copolymer, hydrophobically modified PEGs such as POE(200)-glyceryl-stearate, glucam DOE 120 (PEG 120 Methyl Glucose Dioleate), and Hodag CSA-102 (PEG-150 stearate), and Rewoderm® (PEG modified glyceryl cocoate, palmate or tallowate) from Rewo Chemicals.

Other co-structuring aids which may be used include Amerchol Polymer HM 1500 (Nonoxynyl Hydroethyl Cellulose).

In addition, the inventive bar composition of the invention may include 0 to 15% by wt. optional ingredients as follows: perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise antimicrobials such as 2-hydroxy-4,2',4'trichlorodiphenylether (DP300); preservatives such as dimethyloldimethylhydantoin (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and the like may be used advantageously in amounts of about 0.01% or higher if appropriate.

Cationic polymers as conditioners which may be used include Quatrisoft LM-200 Polyquaternium-24, Merquat Plus 3330 - Polyquaternium 39; and Jaguar® type conditioners.

Polyethylene glycols as conditioners which may be used include:

| | |
|---|---|
| Polyox WSR-205 | PEG 14 M, |
| Polyox WSR-N-60K | PEG 45 M, or |
| Polyox WSR-N-750 | PEG 7 M. |

Another ingredient which may be included are exfoliants such as polyoxyethylene beads, walnut shells and apricot seeds, and the like.

Compositions of the inventive toilet bar also comprise 1% to 13% by wt., preferably 2% to 6% by wt. water.

In one embodiment of the invention, the inventive toilet bar's composition comprises no more than about 60% surfactant and preferably in the range of 5 to 45% by weight.

The emollient "composition" may be a single benefit agent component or it may be a benefit agent compound added via a carrier. Further the benefit agent composition may be a mixture of two or more compounds one or all of which may have a beneficial aspect. In addition, the benefit agent itself may act as a carrier for other components one may wish to add to the bar composition.

A blend of a hydrophobic and hydrophilic emollients may be used. Preferably, hydrophobic emollients are used in excess of hydrophilic emollients in the inventive bar. Most preferably one or more hydrophobic emollients are used alone. Hydrophobic emollients are preferably present in the concentration range of about 0.5 to 40% by weight, more preferably about 15 to 25% by weight. Hydrophillic emollients may preferably be present in the concentration range of 0 to 20% by weight. The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content. Emollients which are either solid or liquid at 25° C. may be used individually or as a blend of emollients with melting points above and below 25° C. It is preferred that at least one emollient has a melting point below 25° C. Preferably the total low melting emollients are present in the concentration range of about 20 to 35% by weight and are hydrophobic.

Useful emollients include the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic and hydrophillic plant extracts;

(e) hydrocarbons such as liquid paraffins, vaseline, microcrystalline wax, ceresin, squalene, pristan and mineral oil;

higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins, minerals, and skin nutrients such as milk, vitamins A, E, and K; vitamin alkyl esters, including vitamin C alkyl esters;

magnesium, calcium, copper, zinc and other metallic components;

(l) sunscreens such as octyl methoxyl cinnamate (Parsol MCX) and butyl methoxy benzoylmethane (Parsol 1789);

(l) phospholipids;

(m) polyhydric alcohols such as glycerine and propylene glycol; and polyols such as polyethylene glycols, (n) antiaging compounds such as alpha hydroxy acids, beta hydroxy acids; and (o) mixtures of any of the foregoing components, and the like.

Preferred emollient benefit agents are selected from triglyceride oils, hydrocarbons, silicone oils, fatty esters, and mixtures thereof. Further preferred emollients are triglycerides having an iodine value from about 50 to about 145, with a range of about 80 to about 130 being especially preferred, including e.g. sunflower seed oil.

The composition may also comprise decorative or functional particulates including speckles, coloured or reflective particles, or shaped particles, encapsulated beads, sponge, and the like.

Conventional art recognised melt cast processing techniques may be used to fabricate the inventive toilet bar. For example, the melted components of the inventive bar are usually blended together at elevated temperatures. Optionally the water level may be adjusted and the blending will continue. Next an optional drying step may follow whereby the water is reduced. Preferably the water level of the ingredients is selected to be low enough to avoid the drying process. Finally, the molten cleansing composition is poured into molds and cooled to its hardening point. The molds may be made of any rigid material that is not subject to attack by the ingredients of the toilet bar. Mold materials may include plastic, metal, glass, ceramic, composite, or elastomeric materials and the like. Cooling the molten cleansing materials can be accomplished by art recognised cooling techniques including refrigeration, cryogenics, ambient air and the like. Controlled cooling using thermostatic control cooling devices may also be employed.

Conventional art recognised packaging materials may be used to package the inventive toilet bar. The package may hold one or more separately packaged bars. Shrink wrap, blister pack, and flow wrap packaging configuration may be used. The package may also have an optional transparent area to view part or all of the bar contained therein. Paper, plastic, or coated paper, or other flexible or rigid packaging materials that are compatible with the toilet bar may be used. Single layer or laminated packaging material structures may also be used. Preferably, the packaging material is moisture proof, and mold resistant. The packaging material should have good barrier properties to prevent the loss of volatile cleansing composition ingredients such as perfume. Examples, of useful barrier materials are polymer coated paper board or other appropriate materials. Hot melt adhesive or contact adhesive such as glue may be used to adhere a portion of the carton and the wrapper. An appropriate coating would be a low density polyethylene coating and the like.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated. Physical test methods are described below:

EXAMPLE 1

Syndet cleansing bars without (bar A) and with lauryl alcohol (bar B) were melt cast from the formulations listed in table 1. Use of lauryl alcohol in the formulation substantially increased the amount of lather as determined using the test method described below. Concentrations are given in parts.

TABLE 1

| | A | B |
|---|---|---|
| Ingredients | | |
| Sodium Cocoyl Isethionate | 23.67 | 22.52 |
| Stearic acid | 6.25 | 5.92 |
| Sodium Isethionate | 0.50 | 0.5 |
| Coco Fatty Acid | 0.60 | 0.6 |
| Alfa Olefin Sulfonate | 7.63 | 7.23 |
| Sodium Lauryl Ether Sulfate (2 EO) | 7.63 | 7.23 |
| Propylene Glycol | 5.27 | 5.00 |
| Glycerin | 4.22 | 4.00 |
| 12-Hydroxystearic acid | 11.60 | 11.00 |
| Lauryl Alcohol | — | 5.00 |
| Sunflower Seed Oil | 26.37 | 25.00 |
| Fragrance | 1.05 | 1.00 |
| Titanium Dioxide | 1.05 | 1.00 |
| Water | 4.00 | 4.00 |
| TOTAL | 99.84 | 100.00 |
| Physical Properties: | | |
| Lather in mls | 26 | 79 |

EXAMPLE 2

Syndet cleansing bars with varying amounts of lauryl alcohol were melt cast from the formulations listed in table 2 and compared to a control (Bar C). Use of lauryl alcohol in the formulation substantially decreased the mush as determined using the test methods described below. Concentrations are given in parts.

TABLE 2

| | C | D | E |
|---|---|---|---|
| Ingredients | | | |
| Sodium Cocoyl Isethionate | 25.02 | 25.02 | 25.02 |
| Stearic acid | 6.58 | 6.58 | 6.58 |
| Sodium Isethionate | 0.55 | 0.55 | 0.55 |
| Coco Fatty Acid | 0.66 | 0.66 | 0.66 |
| Alfa Olefin Sulfonate | 8.00 | 8.00 | 8.00 |
| Sodium Lauryl Ether Sulfate (2 EO) | 8.00 | 8.00 | 8.00 |
| Propylene Glycol | 5.00 | 5.00 | 5.00 |
| Glycerin | 4.00 | 4.00 | 4.00 |
| 12-Hydroxystearic acid | 15.00 | 15.00 | 15.00 |
| Lauryl Alcohol | — | 5.00 | 10.00 |
| Sunflower Seed Oil | 21.01 | 21.01 | 21.01 |
| Fragrance | 1.00 | 1.00 | 1.00 |
| Titanium Dioxide | 1.00 | 1.00 | 1.00 |
| Water | 4.00 | 4.00 | 4.00 |
| Total | 99.82 | 104.82 | 109.82 |
| Physical Properties: | | | |
| Mush | 33.59% | 29.27% | 23.66% |

EXAMPLE 3

Syndet cleansing bars with varying amounts of lauryl alcohol were melt cast from the formulations listed in table 3 and compared to a control (Bar F). Use of higher levels of lauryl alcohol in the formulations were correlated with decreased mush as determined using the test method described below. Concentrations are given in parts.

TABLE 3

| | F | G | H | I |
|---|---|---|---|---|
| Ingredients | | | | |
| Sodium Cocoyl Isethionate | 25.00 | 25.00 | 25.00 | 25.00 |
| Alfa Olefin Sulfonate | 9.00 | 9.00 | 9.00 | 9.00 |
| Sod. Lauryl Ether Sulfate (2EO) | 9.00 | 9.00 | 9.00 | 9.00 |
| Propylene Glycol | 7.00 | 7.00 | 7.00 | 7.00 |
| Glycerin | 7.00 | 7.00 | 7.00 | 7.00 |
| 12-Hydroxy stearic acid | 14.00 | 14.00 | 14.00 | 14.00 |
| Lauryl Alcohol | — | 5.00 | 10.00 | 15.00 |
| Sunflower Seed Oil | 25.00 | 25.00 | 25.00 | 25.00 |
| Water | 4.00 | 4.00 | 4.00 | 4.00 |
| TOTAL | 100.00 | 105.00 | 110.00 | 115.00 |
| Physical Properties: | | | | |
| Mush | 34.1 | 28.2 | 30.8 | 22.3 |

EXAMPLE 4

Cleansing bars with two levels of lauryl alcohol were melt cast from the formulations listed in table 4. Use of the higher levels of lauryl alcohol in the formulations were correlated with decreased mush as determined using the test method described below. Concentrations are given in parts

TABLE 4

| | J | K |
|---|---|---|
| Ingredients | | |
| Sodium Cocoyl Isethionate | 25.00 | 25.00 |
| Alfa Olefin Sulfonate | 9.00 | 9.00 |
| Sodium Lauryl Ether Sulfate (2EO) | 9.00 | 9.00 |
| Propylene Glycol | 7.00 | 7.00 |
| Glycerin | 7.00 | 7.00 |
| Stearic acid | 14.00 | 14.00 |
| Lauryl Alcohol | 5.00 | 10.00 |
| Sunflower Seed Oil | 25.00 | 25.00 |
| Water | 4.00 | 4.00 |
| Total | 105.00 | 110.00 |
| Physical Properties: | | |
| Mush | 36.0 | 30.0 |

EXAMPLE 5

Syndet cleansing bars structured with stearic acid, and containing a high level of triglyceride oil were melt cast with and without lauryl alcohol from the formulations listed in table 5. Surprisingly the use of lauryl alcohol was observed to provide effective emulsification. Without the use of lauryl alcohol, the formulation was thick and opaque and the triglyceride oil separated from the rest of the mass. However a translucent homogeneous melt at 80° C. was obtained with the use of Lauryl alcohol. Concentrations are given in parts.

TABLE 5

| | L | M |
|---|---|---|
| Ingredients | | |
| Sodium Cocoyl Isethionate | 25.00 | 25.00 |
| Alfa Olefin Sulfonate | 9.00 | 9.00 |
| Sodium Lauryl Ether Sulfate (2 EO) | 9.00 | 9.00 |
| Propylene Glycol | 7.00 | 7.00 |

TABLE 5-continued

| | L | M |
|---|---|---|
| Glycerin | 7.00 | 7.00 |
| Stearic acid | 14.00 | 14.00 |
| Lauryl Alcohol | — | 10.00 |
| Sunflower Seed Oil | 25.00 | 25.00 |
| Water | 4.00 | 4.00 |
| Total | 100.00 | 110.00 |

EXAMPLE 6

Syndet cleansing bars containing various inventive and comparative fatty alcohols (used singly or in combination, each at two concentration levels) were melt cast from the base formulation listed in table 6 and their mush and melting points are compared in table 7. Use of the inventive fatty alcohols, i.e. lauryl and oleyl, gave superior mush properties compared to the comparative alcohols.

TABLE 6

| Ingredients | % |
|---|---|
| Sodium Cocoyl Isethionate | 25.02 |
| Stearic Acid | 6.58 |
| Coco Fatty Acids | 0.66 |
| Sodium Isethionate | 0.55 |
| Alfa Olefin Sulfonate | 8.09 |
| Sodium Lauryl Ether Sulfate (2 EO) | 8.09 |
| Fragrance | 1.00 |
| Titanium Dioxide | 1.00 |
| Propylene Glycol | 5.00 |
| Sunflower seed Oil | 21.01 |
| Glycerin | 4.00 |
| 12-Hydroxy Stearic Acid | 15.00 |
| Water | 4.00 |
| Total | 100.00 |

TABLE 7

| # parts Fatty Alcohol | Inventive or Comparative | Mush | MP (C) Fatty Alcohol |
|---|---|---|---|
| No fatty alcohol | | 35.8 | — |
| 5 Oleyl | Inventive | 28.9 | −75 |
| 10 Oleyl | Inventive | 23.2 | |
| 5 Lauryl | Inventive | 26.9 | 24 |
| 10 Lauryl | Inventive | 24.3 | |
| 5 Myristyl | Comparative | 30.5 | 38 |
| 10 Myristyl | Comparative | 28.3 | |
| 5 Cetyl/Stearyl (1:1) | Comparative | 30.5 | 50 |
| 10 Cetyl/Stearyl (1:1) | Comparative | 30.5 | |
| 5 Stearyl (95%) | Comparative | 30.4 | 58 |
| 10 Stearyl (95%) | Comparative | 30.8 | |
| 5 Cetyl (95%) | Comparative | 32.8 | 49 |
| 10 Cetyl (95%) | Comparative | 31.1 | |

Description of Test Methods

Evaluation of Mush:

Immerse a weighed toilet bar in 250 ml water (at 25 ° C.), in a beaker for four hours. Scrape the mush from the bar with a soft plastic knife. Weigh the scraped bar after allowing to dry at room temperature 24 hours. The weight change multiplied by 100 and divided by the initial weight of the bar denotes the mush of the bar. Mush is calculated as the average of three bars.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A cleansing bar composition comprising:

a. an anionic surfactant in the concentration range of about 5 to about 60 weight %;

b. a C6 to C18 free fatty acid in the concentration range of about 2 to about 40 weight %;

c. a fatty alcohol in the concentration of about 2 to about 20 weight %, the alcohol selected from a C6 to C12 alkyl alcohol and a C6 to C18 alkenyl alcohol wherein the melting point of the alcohol is under about 35 ° C.; and wherein said cleansing bar has a mush level less than the bar with the same formulation except without the fatty alcohol.

2. The cleansing bar of claim 1 further comprising a hydrophobic emollient in the concentration range of about 0.5 to about 40 weight %.

3. The cleansing bar of claim 2 wherein the hydrophobic emollient is in the concentration range of about 15 to about 25 weight %.

4. The cleansing bar of claim 1 wherein the anionic surfactant is in the concentration range of about 25 to about 55 weight % and the C6 to C18 free fatty acid is in the concentration range of about 15 to about 25 weight %.

5. The cleansing bar of claim 2 wherein the hydrophobic emollient is selected from triglycerides, hydrocarbons, silicones, fatty esters, and mixtures thereof.

6. The cleansing bar of claim 1 wherein the fatty alcohol is a C6 to C12 alkyl alcohol.

7. The cleansing bar of claim 1 wherein the anionic surfactant includes a C8 to C18 alkali metal acyl isethionate.

8. The cleansing bar of claim 7 wherein the anionic surfactant includes a C8 to C12 alkali metal acyl isethionate.

9. The cleansing bar of claim 7 wherein the alkali metal acyl isethionate is in the concentration range of about 5 to about 45 weight %.

10. The cleansing bar of claim 9 wherein the alkali metal acyl isethionate is in the concentration range of about 15 to about 25 weight %.

11. The cleansing bar of claim 8 wherein the alkali metal acyl isethionate includes sodium cocoyl isethionate.

12. The cleansing bar of claim 1 wherein the free fatty acid includes 12-hydroxy stearic acid.

13. The cleansing bar of claim 12, wherein the 12-hydroxy stearic acid is in the concentration range of about 5 to about 20 weight %.

14. The cleansing bar of claim 12, wherein the concentration range of 12-hydroxy stearic acid is about 10 to about 15 weight %.

15. The cleansing bar of claim 1, wherein the fatty alcohol includes an alcohol selected from lauryl alcohol, oleyl alcohol, and a mixture thereof.

16. The cleansing bar of claim 1, wherein the fatty alcohol is in the concentration range of about 4 to about 8 weight %.

17. The cleansing bar of claim 1, wherein the melting point of the fatty alcohol is under about 25° C.

18. A cleansing bar composition comprising:

a. an anionic surfactant in the concentration range of about 5 to about 60 weight b. a C6 to C18 free fatty acid in the concentration range of about 2 to about 40 weight %; and c. a fatty alcohol selected from a C6 to C12 alkyl alcohol and a C6 to C18 alkenyl alcohol; wherein the melting point of the alcohol is under about 35° C.; and wherein said cleansing bar is formed by a melt cast process.

* * * * *